United States Patent

Treuner et al.

[11] 3,978,050
[45] Aug. 31, 1976

[54] 3-TETRAZOLYL AND OTHER DERIVATIVES OF [[(ALKOXY)THIOCARBONYL]OXY]ACETYL CEPHALOSPORINS

[75] Inventors: Uwe D. Treuner; Hermann Breuer, both of Regensburg, Germany

[73] Assignee: E. R. Squibb & Sons, Inc., Princeton, N.J.

[22] Filed: Jan. 24, 1975

[21] Appl. No.: 544,031

[52] U.S. Cl. .............................. 260/243 C; 424/246
[51] Int. Cl.² ........................................ C07D 501/36
[58] Field of Search ................................ 260/243 C

[56] References Cited
UNITED STATES PATENTS 3,812,116   5/1974   Takano et al. ..................... 260/243 C Primary Examiner—Nicholas S. Rizzo
Assistant Examiner—David E. Wheeler
Attorney, Agent, or Firm—Lawrence S. Levinson; Merle J. Smith

[57] ABSTRACT

3-Heterothio derivatives of [[(alkoxy)thiocarbonyl]oxy]acetyl cephalosporins having the formula

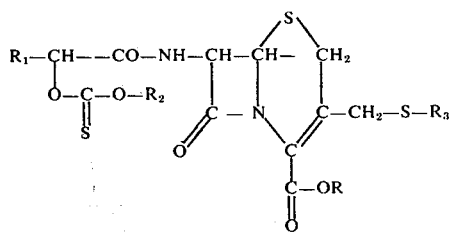

wherein R is hydrogen, lower alkyl, phenyl-lower alkyl, tri(lower alkyl)stannyl, tri(lower alkyl)silyl, a salt forming ion or the group

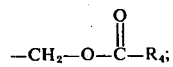

$R_1$ is hydrogen, lower alkyl, phenyl, pyridyl, thienyl or furyl; $R_2$ is lower alkyl or phenyl-lower alkyl; $R_3$ is 1-oxopyridinyl or a five membered heterocycle containing only nitrogen and carbon or nitrogen, carbon and oxygen or sulfur in the ring; $R_4$ is lower alkyl, phenyl or phenyl-lower alkyl; are useful as antibacterial agents.

10 Claims, No Drawings

3-TETRAZOLYL AND OTHER DERIVATIVES OF [[(ALKOXY)THIOCARBONYL]OXY]ACETYL CEPHALOSPORINS

SUMMARY OF THE INVENTION

This invention relates to new 3-heterothio derivatives of [[(alkoxy)thiocarbonyl]oxy]acetylcephalosporins having the formula

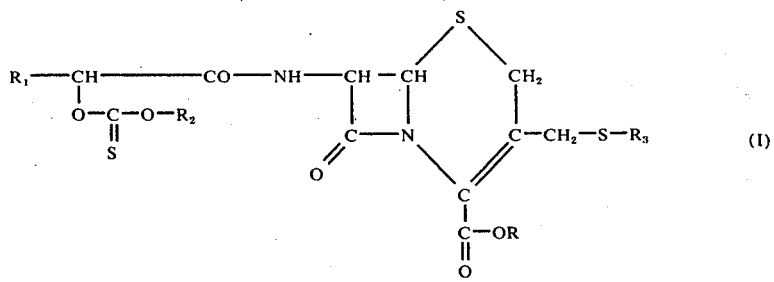

R represents hydrogen, lower alkyl, phenyl-lower alkyl, tri(lower alkyl)stannyl, tri(lower alkyl)silyl, a salt forming ion or the group

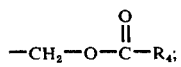

$R_1$ represents hydrogen, lower alkyl, phenyl, pyridyl, thienyl or furyl; $R_3$ represents a five membered heterocyclic ring system of the group including thiadiazolyl, oxadiazolyl, thiatriazolyl, tetrazolyl, or 1-oxopyridinyl; $R_2$ represents lower alkyl or phenyl-lower alkyl; and $R_4$ represents lower alkyl, phenyl or phenyl-lower alkyl. The heterocyclic groups represented by $R_1$ and $R_3$, respectively, optionally bear a lower alkyl group, preferably methyl. They are then $R_5$-pyridyl, $R_5$-thienyl, $R_5$-furyl, $R_5$-thiadiazolyl, $R_5$-oxadiazolyl, $R_5$-tetrazolyl or $R_5$-1-oxypyridinyl, wherein $R_5$ is hydrogen or lower alkyl.

The preferred members within each group are as follows: R is hydrogen, phenyl-lower alkyl, alkali metal, benzhydryl trimethylsilyl or

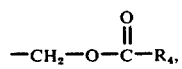

especially hydrogen, methyl, pivaloyloxymethyl, sodium or potassium; $R_1$ is hydrogen, lower alkyl, phenyl or thienyl, especially hydrogen or phenyl; $R_2$ is lower alkyl, especially methyl or ethyl; $R_3$ is (lower alkyl)-thiadiazolyl, especially methylthiadiazolyl, tetrazolyl, (lower alkyl)tetrazolyl, especially methyltetrazolyl; and $R_4$ is methyl or t-butyl.

DETAILED DESCRIPTION OF THE INVENTION

The various groups represented by the symbols have the meanings defined below and these definitions are retained throughout this specification.

The lower alkyl groups are the straight and branched chain hydrocarbon groups in the series from methyl to heptyl, methyl and ethyl being preferred.

The phenyl-lower alkyl radicals include a phenyl ring attached to a lower alkyl group of the kind described above as well as those containing two phenyl groups such as benzhydryl.

The salt forming ions represented by R are metal ions, e.g., alkali metal ions such as sodium or potassium, alkaline earth metal ions such as calcium or magnesium, or an amine salt ion, e.g., a (lower alkyl)amine like methylamine or triethylamine, etc.

The heterocyclic groups represented by $R_3$ are the five membered nitrogen heterocyclics thiadiazole, oxadiazole, thiatriazole, tetrazole, 1-oxopyridine and their lower alkyl substituted analogs including 1,2,4-thiadiazol-5-yl, 1,2,4-thiadiazole-3-yl, 1,3,4-thiadiazol-2-yl, 1,3,4-oxadiazol-2-yl, 1,2,3,4-thiatriazol-5-yl, tetrazolyl, 1-oxopyridinyl as well as these radicals (except thiatriazolyl) bearing a lower alkyl group, especially methyl.

The new 3-heterothio-[[(alkoxy)thiocarbonyl]oxy]acetylcephalosporins of this invention are produced by reacting a 7-aminocephalosporanic acid compound of the formula

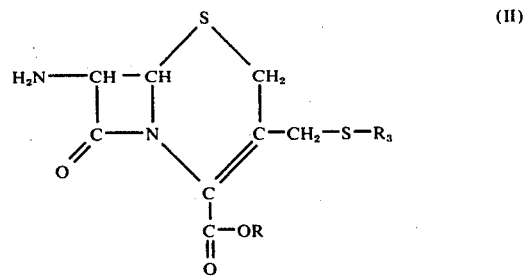

with an [[(alkoxy)thiocarbonyl]oxy]acetic acid of the formula

or an activated derivative of (III).

The activated derivatives referred to include, for example, the reaction product with an anhydride forming reagent such as ethylchloroformate, benzoyl chloride, pivaloyl chloride, etc., or with bis-imidazolecarbonyl, dicyclohexylcarbodiimide, p-nitrophenol or the like.

The reaction between the 7-aminocephalosporanic acid compound and the [[(alkoxy) thiocarbonyl]oxy]acetic acid is effected, for example, by dissolving or suspending the latter or its acid chloride or mixed anhydride in an inert organic solvent such as chloroform, acetone, tetrahydrofuran, methylene chloride, dioxane, benzene or the like, and adding, at a reduced temperature of about 0°–5°C., about an equimolar amount of the 7-ACA compound. An activating compound such as dicyclohexylcarbodiimide may be used. Preferably the compound of formula II is in the form of the benzhydryl ester. The product of the reaction is then isolated by conventional procedures, e.g., by concentration or evaporation of the solvent. The acid chloride is obtained from the acid of formula III by reaction with a chlorinating agent like thionyl chloride. If a derivative of the 7-aminocephalosporanic acid compound, such as the benzhydryl ester is used, the free acid is obtained by hydrolysis, e.g., with trifluoroacetic acid or the like. Salts are then derived from the free acid.

The 7-ACA derivative of formula II is produced by reacting 7-ACA or its derivative (wherein R has the other meanings described above) with a mercaptan HS-$R_3$ at a pH of about 8–8.5. This reaction can also be effected after acylation of 7-ACA with the [[(alkoxy)-thiocarbonyl]oxy]acetic acid of formula III. The starting materials for the latter sequence are described in our copending application Ser. No. 544,033, filed Jan. 24, 1975.

When R is the acyloxymethyl group

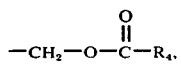

this group is introduced into the 7-aminocephalosporanic acid moiety prior to the reaction with the [[(alkoxy)thiocarbonyl]oxy]acetic acid or the activated derivative by treatment with one to two moles of a halomethyl ester of the formula hal-$CH_2OCOR_4$                   (IV)

wherein hal is halogen, preferably chlorine or bromine, in an inert organic solvent such as dimethylformamide, acetone, dioxane, benzene or the like, at about ambient temperature or below.

The [[(alkoxy)thiocarbonyl]oxy]acetic acid of formula III is produced by forming an ester derivative of an α-hydroxy-acetic acid of the formula

(V)

For example, the benzhydryl ester is formed by reaction with diphenyldiazomethane. The benzhydryl ester of the formula

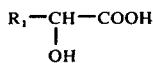

(VI)

is then made to react with thiocarbonylbisimidazole to form the intermediate of the formula

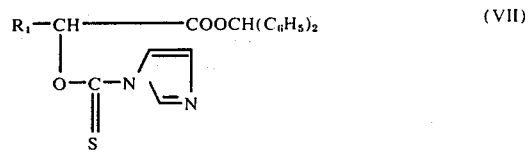

The group —$OR_2$ is introduced by reacting the intermediate of formula VII with an alcohol $R_2$—OH in the presence of sodium imidazole. The benzhydryl group is then removed, e.g., with trifluoroacetic acid and anisole to obtain the free acid of formula III. This is then used for the acylation of the 7-aminocephalosporanic acid compound of formula II.

Further process details are also provided in the illustrative examples.

Certain of the compounds of this invention may exist in different optically active forms. The various stereoisomeric forms as well as the racemic mixtures are within the scope of the invention.

The compounds of this invention have a broad spectrum of antibacterial activity against both gram positive and gram negative organisms such as *Staphylococcus aureus, Salmonella schottmuelleri, Pseudomonas aeruginosa, Proteus vulgaris, Escherichia coli* and *Streptococcus pyogenes*.

They may be used as antibacterial agents in a prophylactic manner, e.g., in cleaning or environmental disinfecting compositions, or otherwise to combat infections due to organisms such as those named above, and in general may be utilized in a manner similar to cephradine and other cephalosporins. For example, a compound of formula I or a physiologically acceptable salt thereof can be used in various animal species in an amount of about 1 to 75 mg/kg, daily, orally or parenterally, in single or two to four divided doses to treat infections of bacterial origin, e.g., 4.0 mg/kg is effective in mice.

Up to about 600 mg. of a compound of formula I or a physiologically acceptable salt thereof can be incorporated in an oral dosage from such as tablet, capsule, elixir, aqueous solution or suspension or the like, or in an injectable form in a sterile aqueous vehicle prepared according to conventional pharmaceutical practice.

The following examples are illustrative of the invention. All temperatures are in degrees celsius. Additional variations are produced in the same manner by appropriate substitution in the starting material.

EXAMPLE 1

α-[(1H-Imidazol-1-yl)thioxomethoxy]benzeneacetic acid, diphenylmethyl ester 12.32 g. (40 mM) of DL-mandelic acid benzhydryl ester are stirred for 6 hours together with 7.12 g. (40 mM) of thiocarbonylbisimidazole in 50 ml. of absolute tetrahydrofuran at room temperature. The reaction mixture is then evaporated, the remaining oil is dissolved in methylene chloride and the solution is washed twice, each with 20 ml. of water. It is then dried over sodium sulfate and evaporated. The remaining oil crystallizes on trituration. The crude product is recrystallized from cyclohexane. 12.1 g. of white crystalline α-[(1H-imidazol-1-yl)thioxomethoxy]benzeneacetic acid, diphenylmethyl ester are obtained, m.p. 109°–110°.

EXAMPLE 2

α-[(Methoxycarbonothioyl)oxy]benzeneacetic acid, diphenylmethyl ester 4.3 g. (10mM) of α[(1H-imidazol-1-yl)thioxomethoxy]-benzeneacetic acid, diphenylmethyl ester together with 0.35 g. of methanol in 30 ml. of dioxane and one drop of a 10% sodium imidazole-dioxane solution, are held at 40° for 5 hours. After drawing off the solvent, the oily residue is dissolved in chloroform and washed three times, each time with 30 ml. of water. After drawing off the solvent, 2.3 g. of α-[(methoxycarbonothioyl)oxy]benzeneacetic acid, diphenylmethyl ester are obtained from the dried chloroform solution in the form of a pale yellow oil which crystallizes after 24 hours. Recrystallization from cyclohexane/petroleum ether yields 1.6 g. of white crystals, m.p. 74°.

EXAMPLE 3

α-[(Methoxycarbonothioyl)oxy]benzeneacetic acid 3.92 g. (10 mM) of the benzhydryl ester from Example 2 are stirred together with 30 ml. of trifluoroacetic acid and a few drops of anisole at 0° for 10 minutes. After distilling the solvent off in vacuum, the residue is treated with petroleum ether until it becomes solid. The solid is then stirred for five minutes in 50 ml. of sodium bicarbonate and filtered. After acidification with 2 N hydrochloric acid and extraction twice, each time with 20 ml. of ether and then drying from the organic phase, 1.2 g. of α-[(methoxycarbonothioyl)oxy]benzeneacetic acid are obtained from the filtrate in the form of white crystals after crystallization from cyclohexane/benzol, m.p. 86°–87°.

EXAMPLE 4

7β-[[[(Methoxycarbonothioyl)oxy]phenylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 2.26 g. (10 mM) of α-[(methoxycarbonothioyl)oxy]-benzeneacetic acid are dissolved in 30 ml. of tetrahydrofuran and, at a temperature of 0° the solution is added to a solution of 2.06 g. of dicyclohexylcarbodiimide in 5 ml. of tetrahydrofuran. After 15 minutes, 4.96 g. (10 mM) of 3-[[(1-methyl-1H-tetrazol-5-yl)thio]methyl]-7-aminocephalosporanic acid, diphenylmethyl ester dissolved in 15 ml. of tetrahydrofuran are added. The mixture is stirred for 18 hours at 0°–5° and the dicyclohexylurea which forms is filtered off. After drawing off the solvent and recrystallizing several times from methylene chloride/petroleum ether/ether, 7β-[[[(methoxycarbonothioyl)oxy]phenylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenyl-methyl, ester is obtained in the form of a beige powder, 3.1 g. m.p. 126°–128°.

EXAMPLE 5

7β-[[[(Methoxycarbonothioyl)oxy]phenylacetyl]amino]-3-[[(1-methyl-1H-tetrazol-5-yl)thio]methyl-8-oxo-5-thia-1-azabicyclo[4.2.0]oct-2-ene-2-carboxylic acid 3 g. (5 mM) of the product from Example 4 are stirred for 15 minutes at 0° in 30 ml. of trifluoroacetic acid. After distilling the trifluoroacetic acid off in vacuum, the remaining oily residue is treated with ether/petroleum ether until it becomes solid. The solid is stirred in 50 ml. of saturated sodium bicarbonate solution and then filtered from the insoluble products. The filtrate is cooled to 5°, a layer of ethyl acetate is added and the whole is acidified to pH 2.5. The aqueous phase is extracted 5 times, each time with 50 ml. of ethyl acetate and after drawing off the solvent, the dried organic phase yields 0.8 g. of the crude 7β-[[[(methoxycarbonothioyl)oxy]phenylacetyl]amino]-3-[[(1-methyl-1H-tetrazol-5-yl)thio]methyl]-8-oxo-5-thia-1-azabicyclo[4.2.0]oct-2-ene-2-carboxylic acid. Recrystallization from tetrahydrofuran/ether and methylene chloride/tetrahydrofuran yields pure product, m.p. 110° (dec.).

EXAMPLE 6

7β-[[[(Methoxycarbonothioyl)oxy]phenylacetyl]amino]-3-[[(1-methyl-1H-tetrazol-5-yl)thio]methyl]-8-oxo-5-thia-1-azabicyclo[4.2.0]oct-2-ene-2-carboxylic acid, potassium salt The potassium salt is obtained as a yellow powder by freeze drying an equimolar aqueous solution of the acid of Example 5 and potassium bicarbonate, m.p. 153°.

EXAMPLE 7

3-[[(5-Methyl-1,3,4-thiadiazole-2-yl)thio]methyl]-7-amino-8-oxo-5-thia-1-azabicyclo[4.2.0]oct-2-ene-2-carboxylic acid A mixture of 13.6 g. (0.05 M) of 7-aminocephalosporanic acid in 100 ml. of water and 50 ml. of acetone are brought to pH 8 with sodium hydroxide while stirring. 9.8 g. (0.57 M) of 2-methyl-1,3,4-thiadiazole-5-thiol are added and the mixture is heated at 80° for 4 hours. After cooling to 5°, this is acidified to pH 3.5 with dilute hydrochloric acid and stirred for 15 minutes. The precipitated solid is filtered under suction and washed with acetone. This 3-[[(5-methyl-1,3,4-thiadiazol-2-yl)thio]methyl]-7-amino-8-oxo-5-thia-1-azabicyclo[4.2.0]oct-2-ene-2-carboxylic acid is purified by dissolving in sodium bicarbonate solution and reprecipitating with 2N hydrochloric acid; yield 12.7 g., m.p. 206°.

EXAMPLE 8

By substituting 3-methyl-1,2,4-thiadiazole-5-thiol for the 2-methyl-1,3,4-thiadiazole-5-thiol in the procedure of Example 7, 11.6 g. of 3-[[(3-methyl-1,2,4-thiadiazol-5-yl)thio]methyl]-7-amino-8-oxo-thia-1-azabicyclo[4.2.0]oct-2-ene-2-carboxylic acid, m.p. 186° (dec.) are obtained.

EXAMPLE 9

By substituting 1-methyl-1H-tetrazole-5-thiol for the 2-methyl-1,3,4-thiadiazole-5-thiol in the procedure of Example 7, 3-[[(1-methyl-1H-tetrazol-5-yl)thio]methyl]-7-amino-8-oxo-5-thia-1-azabicyclo[4.2.0]oct-2-ene-2-carboxylic acid is obtained.

The following additional products are obtained by the procedure of Examples 1, 6 and 7, by substituting for the 2-methyl-1,3,4-thiadiazole-5-thiol in Example 7, the thiol indicated by the 3-substituent, and for the α-[(methoxy-carbonothioyl)oxy]benzeneacetic acid in Example 4, the acid indicated by the substituent:

Example
10  3-[[(1,3,4-thiadiazol-2-yl)thio]methyl-7β-[[[(methoxycarbonothioyl)oxy]phenylacetyl]-

Example amino]-8-oxo-5-thia-1-azabicyclo[4.2.0]oct-2-ene-2-carboxylic acid.
11  3-[[(1,3,4-thiadiazol-2-yl)thio]methyl]-7β-[[[(ethoxycarbonothioyl)oxy]phenylacetyl]amino]-8-oxo-5-thia-1-azabicyclo[4.2.0]oct-2-ene-2-carboxylic acid.
12  3-[[(5-ethyl-1,3,4-thiadiazol-2-yl)thio]methyl]-7β-[[[(n-butoxycarbonothioyl)oxy]phenylacetyl]amino]-8-oxo-5-thia-1-azabicyclo[4.2.0]oct-2-ene-2-carboxylic acid and sodium salt.
13  3-[[5-methyl-1,3,4-thiadiazol-2-yl)thio]methyl]-7β-[[(methoxycarbonothioyl)oxy]acetylamino]-8-oxo-5-thia-1-azabicyclo[4.2.0]oct-2-ene-2-carboxylic acid and potassium salt.
14  3-[[(1,2,3,4-thiatriazol-5-yl)thio]methyl]-7β-[[[(methoxycarbonothioyl)oyl]phenylacetyl]amino]-8-oxo-5-thia-1-azabicyclo[4.2.0]oct-2-ene-2-carboxylic acid.
15  3-[[(1,2,3,4-thiatriazol-5-yl)thio]methyl]-7β-[[[(ethoxycarbonothioyl)oxy]-2-(2-thienyl)acetyl]amino]-8-oxo-5-thia-1-azabicyclo[4.2.0]oct-2-ene-2-carboxylic acid.
16  3-[[(1,2,3,4-thiatriazol-5-yl)thio]methyl]-7β-[[[(methoxycarbonothioyl)oxy]acetyl]amino]-8-oxo-5-thia-1-azabicyclo[4.2.0]oct-2-ene-2-carboxylic acid.
17  3-[[(1H-tetrazol-5-yl)thio]methyl]-7β-[[[(benzyloxycarbonothioyl)oxy]phenylacetyl]amino]-8-oxo-5-thia-1-azabicyclo[4.2.0]oct-2-ene-2-carboxylic acid.
18  3-[[(1-ethyl-1H-tetrazol-5-yl)thio]methyl]-7β-[[[(methoxycarbonothioyl)oxy]acetyl]amino]-8-oxo-5-thia-1-azabicyclo[4.2.0]oct-2-ene-2-carboxylic acid, trimethylsilyl ester.
19  3-[[(1,2,3,4-thiatriazol-5-yl)thio]methyl]-7β-[[[(methoxycarbonothioyl)oxy] -2-(2-furyl)acetyl]amino]-8-oxo-5-thia-1-azabicyclo[4.2.0]oct-2-ene-2-carboxylic acid.
20  3-[[(5-methyl-1,3,4-thiadiazol-2-yl)thio]methyl]-7β-[[[(methoxycarbonothioyl)oxy]-2-(2-pyridyl)acetyl]amino]-8-oxo-5-thia-1-azabicyclo[4.2.0]oct-2-ene-2-carboxylic acid and potassium salt.
21  30[[(1,2,4-thiadiazol-5-yl)thio]methyl]-7β-[[[(n-propoxycarbonothioyl)oxy]acetyl]amino]-8-oxo-5-thia-1-azabicyclo[4.2.0]oct-2-ene-2-carboxylic acid, trimethylsilyl ester.
22  3-[[(1,2,4-thiadiazol-3-yl)thio]methyl]-7β-[[[(phenylethoxycarbonothioyl)oxy]phenylacetyl]amino]-8-oxo-5-thia-1-azabicyclo[4.2.0]oct-2-ene-2-carboxylic acid.
23  3-[[(5-butyl-1,2,4-thiadiazol-3-yl)thio]methyl]-7β-[[[(methoxycarbonothioyl)oxy]acetyl]amino]-8-oxo-5-thia-1-azabicyclo[4.2.0]oct-2-ene-2-carboxylic acid.
24  3-[[(1-ethyl-1H-tetrazol-5-yl)thio]methyl]-7β-[[[(ethoxycarbonothioyl)oxy]-2-(2-pyridyl)acetyl]amino]-8-oxo-5-thia-1-azabicyclo[4.2.0]oct-2-ene-2-carboxylic acid and potassium salt.
25  3-[[(1H-tetrazol-5-yl)thio]methyl]-7β-[[[(methoxycarbonothioyl)oxy]acetyl]amino]-8-oxo-5-thia-1-azabicyclo[4.2.0]oct-2-ene-2-carboxylic acid.
26  3-[[(1-methyl-1H-tetrazol-5-yl)thio]methyl]-7β-[[[(ethoxycarbonothioyl)oxy]-2-(2-furyl)acetyl]amino]-8-oxo-5-thia-1-azabicyclo[4.2.0]oct-2-ene-2-carboxylic acid and potassium salt.
27  3-[[(1-methyl-1H-tetrazol-5-yl)thio]methyl]-7β-[[[(methoxycarbonothioyl)oxy]-2-(3-thienyl)acetyl]amino]-8-oxo-5-thia-1-azabicyclo[4.2.0]oct-2-ene-2-carboxylic acid pivaloyloxymethyl ester.
28  3-[[(1-ethyl-1H-tetrazol-5-yl)thio]methyl]-7β-[[[(ethoxycarbonothioyl)oxy]acetyl]amino]]-8-oxo-5-thia-1-azabicyclo[4.2.0]oct-2-ene-2-carboxylic acid.
29  3-[[(1H-tetrazol-5-yl)thio]methyl]-7β-[[(n-butoxycarbonothioyl)oxy]acetyl]amino]-8-oxo-5-thia-1-azabicyclo[4.2.0]oct-2-ene-2-carboxylic acid and phenylacetoxymethyl ester.
30  3-[[(3-methyl-1,2,4-thiadiazol-5-yl)thio]methyl]-7β-[[[(methoxycarbonothioyl)oxy]phenylacetyl]amino]-8-oxo-5-thia-1-azabicyclo[4.2.0]oct-2-ene-2-carboxylic acid.
31  3-[[(1,2,4-thiadiazol-3-yl)thio]methyl]-7β-[2-[[(phenylethoxycarbonothioyl)oxy]propionyl]amino]-8-oxo-5-thia-1-azabicyclo[4.2.0]oct-2-ene-2-carboxylic acid pivaloyloxymethyl ester.
32  3-[[(1H-tetrazol-5-yl)thio]methyl]-7β-[2-[[(ethoxycarbonothioyl)oxy]propionyl]amino]-8-oxo-5-thia-1-azabicyclo[4.2.0]oct-2-ene-2-carboxylic acid.
33  3-[[(1-methyl-1H-tetrazol-5-yl)thio]methyl]-7β-

Example

[2-[[(methoxycarbonothioyl)oxy]butyryl]amino]-8-oxo-5-thia-1-azabicyclo[4.2.0]oct-2-ene-carboxylic acid and potassium salt.
34  3-[[(1-oxopyridin-2-yl)thio]methyl]-7β-[[[(methoxycarbonothioyl)oxy]phenylacetyl]amino]-8-oxo-5-thia-1-azabicyclo[4.2.0]oct-2-ene-2-carboxylic acid.
35  3-[[(4-methyl-1-oxopyridin-2-yl)thio]methyl]-7β-[2-[[(methoxycarbonothioyl)oxy]propionyl]amino]-8-oxo-5-thia-1-azabicyclo[4.2.0]oct-2-ene-2-carboxylic acid and sodium salt.
36  3-[[(1,3,4-oxadiazol-2-yl)thio]methyl]-7β-[[[(methoxycarbonothioyl)oxy]phenylacetyl]amino]-8-oxo-5-thia-1-azabicyclo[4.2.0]oct-2-ene-2-carboxylic acid.
37  3-[[5-methyl-1,3,4-oxadiazol-2-yl)thio]methyl]-7β-[2-[[(methoxycarbonothioyl)oxy]n-butyryl]amino]-8-oxo-5-thia-1-azabicyclo[4.2.0]oct-2-ene-2-carboxylic acid.

What is claimed is:
1. A compound of the formula

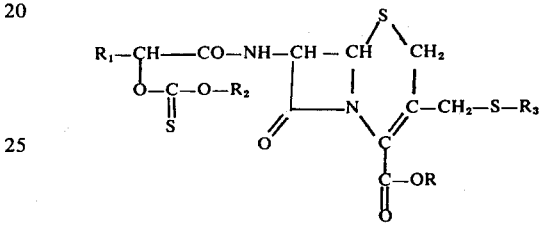

wherein R is hydrogen, lower alkyl, phenyl-lower alkyl, tri(lower alkyl)stannyl, tri(lower alkyl)silyl, —CH$_2$OCO—R$_4$, alkali metal, alkaline earth metal or lower alkylamine; R$_1$ is hydrogen, lower alkyl, phenyl, R$_5$-pyridyl, R$_5$-thienyl or R$_5$-furyl; R$_2$ is lower alkyl or phenyl-lower alkyl; R$_3$ is a five membered herterocyclic of the group R$_5$-thiadiazole, thiatriazole, R$_5$-tetrazole, R$_4$ is lower alkyl, phenyl or phenyl-lower alkyl; and R$_5$ is hydrogen or lower alkyl.
2. A compound as in claim 1 wherein R is hydrogen, phenyl-lower alkyl, alkali metal, benzhydryl, trimethylsilyl

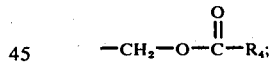

R$_1$ is hydrogen, lower alkyl, phenyl or thienyl; R$_2$ is lower alkyl; R$_3$ is (lower alkyl)thiadiazole, tetrazole or (lower alkyl)tetrazole; and R$_4$ is methyl or t-butyl.
3. A compound as in claim 1 wherein R$_1$ is phenyl.
4. A compound as in claim 3 wherein R$_2$ is lower alkyl and R$_3$ is (lower alkyl)tetrazole.
5. A compound as in claim 4 wherein each lower alkyl group is methyl.
6. A compound as in claim 1 wherein R$_3$ is 1-lower alkyl-1H-tetrazol-5-yl.
7. A compound as in claim 1 wherein R is hydrogen, R$_1$ is phenyl, R$_2$ is methyl and R$_3$ is 1-methyl-1H-tetrazol-5-yl.
8. Alkali metal salt of the compound of claim 7.
9. A compound as in claim 8 wherein the alkali metal is potassium.
10. A compound as in claim 1 wherein R is hydrogen, R$_1$ is phenyl, R$_2$ is methyl and R$_3$ is 3-methyl-1,2,4-thiadiazol-5-yl.

* * * * *

UNITED STATES PATENT OFFICE
CERTIFICATE OF CORRECTION

PATENT NO. : 3,978,050
DATED : August 31, 1976
INVENTOR(S) : Uwe D. Treuner, Hermann Breuer It is certified that error appears in the above-identified patent and that said Letters Patent are hereby corrected as shown below:

Column 8, line 36 in claim 1 after "thiatriazole" should be inserted -- $R_5$-oxadiazole --.

Signed and Sealed this twelfth Day of July 1977

[SEAL]

Attest:

RUTH C. MASON
Attesting Officer

C. MARSHALL DANN
Commissioner of Patents and Trademarks